(12) United States Patent
Rubinsky et al.

(10) Patent No.: US 12,209,318 B2
(45) Date of Patent: *Jan. 28, 2025

(54) METHODS, SYSTEMS, AND APPARATUSES FOR DELIVERY OF ELECTROLYSIS PRODUCTS

(71) Applicant: RM2 TECHNOLOGY LLC, Miami, FL (US)

(72) Inventors: Boris Rubinsky, El Cerrito, CA (US); Paul Mikus, Coto de Caza, CA (US); Liel Rubinsky, El Cerrito, CA (US)

(73) Assignee: RM2 TECHNOLOGY LLC, Miami, FL (US)

( * ) Notice: Subject to any disclaimer, the term of this patent is extended or adjusted under 35 U.S.C. 154(b) by 82 days.

This patent is subject to a terminal disclaimer.

(21) Appl. No.: 17/553,401

(22) Filed: Dec. 16, 2021

(65) Prior Publication Data
US 2022/0105256 A1    Apr. 7, 2022

Related U.S. Application Data

(60) Division of application No. 16/219,815, filed on Dec. 13, 2018, now Pat. No. 11,260,165, which is a
(Continued)

(51) Int. Cl.
*C25B 1/26*    (2006.01)
*A61B 18/02*    (2006.01)
(Continued)

(52) U.S. Cl.
CPC ............... *C25B 1/26* (2013.01); *A61B 18/02* (2013.01); *A61B 18/04* (2013.01); *A61B 18/12* (2013.01);
(Continued)

(58) Field of Classification Search
CPC .................................. C25B 1/26; C25B 9/17
See application file for complete search history.

(56) References Cited

U.S. PATENT DOCUMENTS

| | | | |
|---|---|---|---|
| 5,389,069 | A | 2/1995 | Weaver et al. |
| 5,468,223 | A | 11/1995 | Mir |

(Continued)

FOREIGN PATENT DOCUMENTS

| | | | |
|---|---|---|---|
| EP | 2311522 A1 | 4/2011 | |
| EP | 2425871 A2 | 3/2012 | |

(Continued)

OTHER PUBLICATIONS

Extended European Search Report for Application No. EP19857135.8, mailed on Apr. 13, 2022, 07 pages.
(Continued)

*Primary Examiner* — Kevin Joyner
(74) *Attorney, Agent, or Firm* — Stoel Rives LLP

(57) ABSTRACT

Example apparatuses and systems are disclosed for providing controlled delivery of electrolysis products to a site which may be used for treatment of infection and ablation of undesirable cells and tissue. A system disclosed may include a power supply, two electrodes, an aqueous matrix that may close the electric circuit between the electrodes at the treated site, and a controller. The controller may control the electrical circuit to induce a direct current through the electrodes and an aqueous matrix to produce electrolysis products. The duration and magnitude of the charge applied may determine the dose of the products applied to the treatment site. The composition of the electrodes and the aqueous matrix may be chosen to produce desired products. An apparatus is disclosed that may be in the form of a pad for applying to a wound. An apparatus is disclosed that may be used for treating internal tissue.

25 Claims, 10 Drawing Sheets

US 12,209,318 B2
Page 2

Related U.S. Application Data continuation of application No. 15/036,386, filed as application No. PCT/US2014/065783 on Nov. 14, 2014, now Pat. No. 10,154,873.

(60) Provisional application No. 61/938,623, filed on Feb. 11, 2014, provisional application No. 61/921,084, filed on Dec. 27, 2013, provisional application No. 61/904,142, filed on Nov. 14, 2013.

(51) Int. Cl.
*A61B 18/04* (2006.01)
*A61B 18/12* (2006.01)
*A61B 18/14* (2006.01)
*A61M 1/00* (2006.01)
*A61M 25/10* (2013.01)
*A61N 1/05* (2006.01)
*A61N 1/32* (2006.01)
*C25B 9/17* (2021.01)
*C25B 11/04* (2021.01)
*A61B 18/00* (2006.01)
*A61B 18/16* (2006.01)

(52) U.S. Cl.
CPC ......... *A61B 18/1492* (2013.01); *A61M 1/916* (2021.05); *A61M 25/104* (2013.01); *A61N 1/0502* (2013.01); *A61N 1/32* (2013.01); *A61N 1/325* (2013.01); *A61N 1/327* (2013.01); *C25B 9/17* (2021.01); *C25B 11/04* (2013.01); *A61B 2018/00333* (2013.01); *A61B 2018/00404* (2013.01); *A61B 2018/00434* (2013.01); *A61B 2018/00452* (2013.01); *A61B 2018/00464* (2013.01); *A61B 2018/00482* (2013.01); *A61B 2018/00517* (2013.01); *A61B 2018/00547* (2013.01); *A61B 2018/00577* (2013.01); *A61B 2018/00613* (2013.01); *A61B 2018/00827* (2013.01); *A61B 2018/00892* (2013.01); *A61B 2018/1425* (2013.01); *A61B 2018/143* (2013.01); *A61B 18/16* (2013.01); *A61M 2025/105* (2013.01); *A61M 2025/1052* (2013.01); *A61M 2205/054* (2013.01); *A61M 2205/52* (2013.01)

(56) References Cited

U.S. PATENT DOCUMENTS

| | | | |
|---|---|---|---|
| 5,911,223 | A | 6/1999 | Weaver et al. |
| 6,300,108 | B1 | 10/2001 | Rubinsky et al. |
| 6,366,808 | B1 | 4/2002 | Schroeppel et al. |
| 6,403,348 | B1 | 6/2002 | Rubinsky et al. |
| 6,767,347 | B2 * | 7/2004 | Sharkey ............ A61B 18/1492 606/41 |
| 7,113,821 | B1 | 9/2006 | Sun et al. |
| 7,344,533 | B2 | 3/2008 | Pearson et al. |
| 7,680,543 | B2 | 3/2010 | Azure |
| 7,718,409 | B2 | 5/2010 | Rubinsky et al. |
| 7,955,827 | B2 | 6/2011 | Rubinsky et al. |
| 8,048,067 | B2 | 11/2011 | Davalos et al. |
| 8,145,316 | B2 | 3/2012 | Deem et al. |
| 8,282,631 | B2 | 10/2012 | Davalos et al. |
| 8,849,413 | B2 | 9/2014 | Makdissi |
| 8,926,606 | B2 | 1/2015 | Davalos et al. |
| 9,005,189 | B2 | 4/2015 | Davalos et al. |
| 9,283,051 | B2 | 3/2016 | Garcia et al. |
| 9,700,368 | B2 | 7/2017 | Callas et al. |
| 9,901,735 | B1 | 2/2018 | Lee et al. |
| 10,154,873 | B2 | 12/2018 | Rubinsky et al. |
| 10,390,874 | B2 | 8/2019 | Rubinsky et al. |
| 10,939,949 | B2 | 3/2021 | Rubinsky et al. |
| 11,123,475 | B2 | 9/2021 | Rubinsky et al. |
| 11,260,165 | B2 | 3/2022 | Rubinsky et al. |
| 11,857,244 | B2 | 1/2024 | Rubinsky et al. |
| 11,866,833 | B2 | 1/2024 | Rubinsky et al. |
| 2001/0021868 | A1 | 9/2001 | Herbst et al. |
| 2002/0010491 | A1 | 1/2002 | Schoenbach et al. |
| 2002/0143365 | A1 | 10/2002 | Herbst |
| 2003/0042134 | A1 | 3/2003 | Tremblay et al. |
| 2004/0213698 | A1 | 10/2004 | Tennakoon et al. |
| 2006/0116663 | A1 | 6/2006 | Joshi et al. |
| 2006/0293731 | A1 | 12/2006 | Rubinsky et al. |
| 2008/0167650 | A1 | 7/2008 | Joshi et al. |
| 2009/0287208 | A1 | 11/2009 | Rosenberg |
| 2010/0030211 | A1 | 2/2010 | Davalos et al. |
| 2010/0036446 | A9 | 2/2010 | Auge et al. |
| 2010/0168646 | A1 | 7/2010 | Greenbaum et al. |
| 2010/0183745 | A1 | 7/2010 | Rossi et al. |
| 2011/0106072 | A1 | 5/2011 | Sundquist et al. |
| 2012/0059255 | A1 | 3/2012 | Paul et al. |
| 2012/0071874 | A1 | 3/2012 | Davalos et al. |
| 2012/0130369 | A1 | 5/2012 | Cadossi et al. |
| 2012/0150173 | A1 | 6/2012 | Joshi et al. |
| 2012/0220998 | A1 | 8/2012 | Long et al. |
| 2013/0218157 | A1 | 8/2013 | Callas et al. |
| 2014/0066913 | A1 | 3/2014 | Sherman |
| 2014/0276767 | A1 | 9/2014 | Brotz et al. |
| 2014/0316485 | A1 | 10/2014 | Ackermann et al. |
| 2016/0184003 | A1 | 6/2016 | Srimathveeravalli et al. |
| 2016/0287867 | A1 | 10/2016 | Rubinsky et al. |
| 2016/0296269 | A1 | 10/2016 | Rubinsky et al. |
| 2018/0193082 | A1 | 7/2018 | Rubinsky et al. |
| 2019/0117291 | A1 | 4/2019 | Rubinsky et al. |
| 2019/0357960 | A1 | 11/2019 | Rubinsky et al. |
| 2021/0186592 | A1 | 6/2021 | Rubinsky et al. |
| 2021/0220532 | A1 | 7/2021 | Rubinsky et al. |
| 2021/0330371 | A1 | 10/2021 | Günther et al. |

FOREIGN PATENT DOCUMENTS

| | | |
|---|---|---|
| EP | 1696812 B1 | 7/2015 |
| WO | 03103521 A1 | 12/2003 |
| WO | 2007070637 A2 | 6/2007 |
| WO | 2015021113 A1 | 2/2015 |
| WO | 2015073877 A1 | 5/2015 |
| WO | 2015073885 A1 | 5/2015 |
| WO | 2016178697 A1 | 11/2016 |
| WO | WO-2017143269 A1 | 8/2017 |
| WO | WO-2020051241 A1 | 3/2020 |

OTHER PUBLICATIONS

Extended European Search Report for Application No. EP21212300.4, mailed on Apr. 25, 2022, 09 pages.
Lv Y., et al., "Molecular and Histological Study on the Effects of Electrolytic Electroporation on the Liver," Bioelectrochemistry, Feb. 2019, vol. 125, pp. 79-89.
The Extended European Search Report dated Jan. 17, 2022 for European Patent Application No. 21212317.8.
Examination Report dated Mar. 19, 2018 for European Application No. 14862428.1.
Examination Report dated Mar. 19, 2018 for European Application No. 14862589.0.
International Search Report & Written Opinion dated Apr. 21, 2015 received for PCT/US2014/065794.
International Search Report and Written Opinion Received for PCT/US2014/065783 dated Mar. 18, 2015.
Office Action for CN Application No. 201580080597.8, dated May 7, 2020.
Office Action for EP Application No. 14862428.1, dated Dec. 16, 2020.
Office Action for EP Application No. 14862589.0, dated Dec. 11, 2020.
"International Search Report and Written Opinion received for PCT US2015/030628 dated Jan. 15, 2016".
"Receipt of extended EP search report for application No. 14862428.1 dated May 10, 2017".

(56) References Cited

OTHER PUBLICATIONS

"Receipt of extended EP search report for application No. 14862589.0 dated May 10, 2017".
Ivorra, et al., "Electric Field Modulation in Tissue Electroporation With Electrolytic and Non-Electrolytic Additives", Bioelectrochemistry 70, Feb. 2007, pp. 551-560.
Ivorra, et al., "In Vivo Electrical Impedance Measurements During and After Electroporation of Rat Liver", Bioelectrochemistry 70, Oct. 2006, pp. 287-295.
Mir, et al., "Mechanisms of Electrochemotherapy", Advanced Drug Delivery Reviews, vol. 35, No. 1, Jan. 1, 1999, XP055754391, Amsterdam, NL, pp. 107-118.
Czymek R., et al., "Electrochemical Treatment. An Investigation of Dose-response Relationships Using an Isolated Liver Perfusion Model," Saudi Journal of Gastroenterology : Official Journal of the Saudi Gastroenterology Association, vol. 17 (5), 2011, pp. 335-343.
Davalos R.V., et al., "Tissue Ablation With Irreversible Electroporation," Annals of Biomedical Engineering vol. 33 (2), Feb. 2005, pp. 223-231.
Edd Jon F., et al., "In Vivo Results of a New Focal Tissue Ablation Technique : Irreversible Electroporation," IEEE Transactions on Bio-medical Engineering vol. 53 (5), Jul. 2006, pp. 1409-1415.
Fosh B.G., et al., "Electrolytic Ablation of the Rat Pancreas. A Feasibility Trial," BMC Gastroenterology, vol. 1, 2001, pp. 1-5.
Gravante G., et al., "Experimental Application of Electrolysis in the Treatment of Liver and Pancreatic Tumours: Principles, Preclinical and Clinical Observations and Future Perspectives," Surgical Oncology vol. 20 (2), Jun. 2011, pp. 106-120.
Guenther E., et al., "Electrical Breakdown in Tissue Electroporation," Biochemical and Biophysical Research Communications, vol. 467 (4), Nov. 2015, pp. 1-14.
Horwitz E.M., et al., "Definitions of Biochemical Failure That Best Predict Clinical Failure in Patients with Prostate Cancer Treated with External Beam Radiation Alone: a Multi-institutional Pooled Analysis," The Journal of Urology vol. 173 (3), Mar. 2005, pp. 797-802.
Klein N., et al., "Single Exponential Decay Waveform; a Synergistic Combination of Electroporation and Electrolysis (E2) for Tissue Ablation," Peer-Reviewed Journal, vol. 5. Apr. 2017, pp. 1-19.
Klein N., et al., "The Combination of Electroportation and Electrolysis (E2) Employing Different Electrode Arrays for Ablation of Large Tissue Volumes," PLoS ONE vol. 14 (8), Aug. 2019, pp. 1-13.
Llyod M., et al., "Electrolysis—a New Method of Renal Ablation?," BJU International, vol. 110 (Suppl 4), Dec. 2012, pp. 77-79.
MacLaren J. S., "Electrolysis in Prostate Enlargement," Annals of Surgery vol. 9 (5), May 1889, pp. 347-350.
Martin R.C.G., et al., "Intra-Operative Anesthesia Management in Patients Undergoing Surgical Irreversible Electroporation of the Pancreas, Liver, Kidney, and Retroperitoneal Tumors," Anesthesiology and Pain Medicine , vol. 5 (3), Jun. 2015, pp. 1-8.

Mir L.M., et al., "The Basis of Electrochemotherapy," Methods in Molecular Medicine, vol. 37, 2000, pp. 99-117.
Neumann E., et al., "Electroporation and Electrofusion in Cell Biology," Plenum Press, New York, 1989, pp. 1-435.
Neumann E., et al., "Gene Transfer Into Mouse Lyoma Cells by Electroporation in High Electric Fields," The EMBO Journal 1(7), 1982, pp. 841-845.
Onik G., et al., "Irreversible Electroporation: First Patient Experience Focal Therapy of Prostate Cancer," Irreversible Electroporation. Series in Biomedical Engineering Springer-Verlag Berlin Heidelberg, Berlin, Heidelberg, 2010, pp. 235-247.
Phillips M., et al., "Combining Electrolysis and Electroporation for Tissue Ablation," Technology in Cancer Research & Treatment, Aug. 2015, vol. 14 (4), pp. 395-410.
Phillips M., et al., "Modulating Electrolytic Tissue Ablation With Reversible Electroporation Pulses," Technology, vol. 3 (1), 2015, pp. 45-53.
Phillips M., et al., "Tissue Ablation by a Synergistic Combination of Electroporation and Electrolysis Delivered by a Single Pulse," Annals of Biomedical Engineering, vol. 44 (10), Oct. 2016, pp. 3144-3154.
Robertson G.S., et al., "Experimental Study of Electrolysis-induced Hepatic Necrosis," The British Journal of Surgery, Sep. 1998, vol. 85 (9), pp. 1212-1216.
Rubinsky B., et al., "Irreversible Electroporation: A New Ablation Modality—clinical Implications," Technology in Cancer Research & Treatment, Feb. 2007, vol. 6 (1), pp. 37-48.
Rubinsky B., et al., "Minimally Invasive, Non-Thermal Tissue Ablation with a Single Exponential Decay Electrolytic Electroporation Waveform," Journal of Translational Medicine and Research, vol. 21 (4), 2016, pp. 247-252.
Rubinsky L., et al., "Electrolytic Effects During Tissue Ablation by Electroporation," Technology in Cancer Research & Treatment, Oct. 2016, vol. 15(5), pp. 1-9.
Scheffer H., et al., "Irreversible Electroporation for Colorectal Liver Metastases ," Techniques in Vascular and Interventional Radiology, Sep. 2015, vol. 18 (3), pp. 159-169.
Stehling K.M., et al., "Synergistic Combination of Electrolysis and Electroporation for Tissue Ablation," PloS One, vol. 11 (2), 2016, pp. 1-23.
Tasu J.P., et al., "Irreversible Electroporation for Locally Advanced Pancreatic Cancer: Where Do We Stand in 2017?," Pancreas, Mar. 2017, vol. 46(3), pp. 283-287.
Weaver J.C. and Chizmadzhev Y.A., "Theory of Electroporation: A Review," Bioelectrochemistry and Bioenergetics, Mar. 1996, vol. 41 (2), pp. 135-160.
Denet A., et al., "Transdermal Delivery of Timolol by Electroporation Through Human Skin," Journal of Controlled Release, Mar. 2003, vol. 88(2), pp. 253-262.
Saulis G., et al., "Changes of the Solution PH Due to Exposure by High-voltage Electric Pulses," Bioelectrochemistry, Sep. 2005, vol. 67(1), pp. 101-108.

* cited by examiner

METHODS, SYSTEMS, AND APPARATUSES FOR DELIVERY OF ELECTROLYSIS PRODUCTS

CROSS-REFERENCE TO RELATED APPLICATIONS

This application is a divisional application of U.S. application Ser. No. 16/219,815, filed on Dec. 13, 2018, which is a continuation of U.S. application Ser. No. 15/036,386, filed May 12, 2016 and issued as U.S. Pat. No. 10,154,873, on Dec. 18, 2018, which is a national stage application of PCT Application No. PCT/US2014/065783, filed Nov. 14, 2014, which claims priority to provisional applications U.S. Ser. No. 61/904,142 filed on Nov. 14, 2013, U.S. Ser. No. 61/921,084 filed on Dec. 27, 2013, and U.S. Ser. No. 61/938,623 filed on Feb. 11, 2014.

The entire disclosures of the afore-mentioned applications are considered to be part of the disclosure of the instant application and are hereby incorporated by reference in their entirety for any purpose.

BACKGROUND

Electrolysis generally refers to a process of inducing an electrochemical reaction that involves passing a direct current through an ionic solution via electrodes. Electrolysis may facilitate the removal and/or addition of electrons from atoms and/or ions, which may lead to the formation of new products. For example, by passing a DC current through a saline solution (NaCl and $H_2O$), hypochlorous acid (HClO) may be formed.

Hypochlorous acid has disinfecting properties and is often used as a cleaning agent. In some applications, hypochlorous acid is used to ablate unwanted tissue and/or disinfect wounds in tissue. Hypochlorous acid is typically introduced to the wound by pouring a solution of hypochlorous acid over the wound or soaking a wound dressing in hypochlorous acid and applying the dressing to the wound.

When exposed to air, hypochlorous acid decomposes over time. As the acid breaks down, the disinfecting and ablation properties are decreased. To maintain effectiveness, fresh hypochlorous acid is poured over the wound and/or the soaked gauze is replaced at multiple intervals. The labor intensive nature of continuingly treating wounds to ensure effectiveness of disinfection as well as the lack of precision in delivering the hypochlorous acid may make this mode of use of hypochlorous acid impractical in emergency and clinical environments.

SUMMARY

An example apparatus for delivery of electrolysis products to a site according to an embodiment of the disclosure may include an electrode, an aqueous matrix in contact with the electrode, wherein the aqueous matrix may include a saline solution, wherein the electrode may include a material and the aqueous matrix may have a pH, the material and the pH may be selected to produce the electrolysis products when a current is passed through the aqueous matrix using the electrode, and wherein the electrode and the aqueous matrix may be packaged for placement proximate the site.

An example system for delivery of electrolysis products to a site may include a device which may be positioned proximate the site, wherein the device may include an electrode and an aqueous matrix, a power supply, a controller which may be positioned at the site or remotely from the site, the controller may be in communication with the electrical circuit, and wherein the controller may be programmed to provide an electronic signal to the circuit for the electrode to produce the electrolysis products, wherein the electronic signal may be indicative of a dose of the electrolysis products and the timing of the production of the dose.

An example method for delivering electrolysis products to a site may include using a controller remote from the site, generating an electrical signal indicative of a timing and dose of the electrolysis products, providing the electrical signal to a device proximate the site, wherein the device is configured to generate the electrolysis products responsive to the electrical signal.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which

DETAILED DESCRIPTION

Certain details are set forth below to provide a sufficient understanding of embodiments of the disclosure. However, it will be clear to one skilled in the art that embodiments of the disclosure may be practiced without these particular details. Moreover, the particular embodiments of the present disclosure described herein are provided by way of example and should not be used to limit the scope of the invention to these particular embodiments. In other instances, well-known materials, components, processes, controller components, software, circuitry, timing diagrams, and/or anatomy have not been described or shown in detail in order to avoid unnecessarily obscuring the embodiments.

In some embodiments, electrolysis products, such as hypochlorous acid, may be used for disinfecting and/or ablation. The products may be produced and delivered in a controlled manner to maintain effectiveness. In some embodiments, a system and/or apparatus may include a solution capable of producing, upon electrolysis, sterilizing products. The solution may be brought into contact with the tissue to be treated. Electrodes capable of producing electrolysis may be brought into contact with the solution, and an electric current may be generated in the solution that produces the desired levels of electrolysis products. The magnitude and duration of the current generated may be controlled to modulate the amount of products produced.

Figure 1:
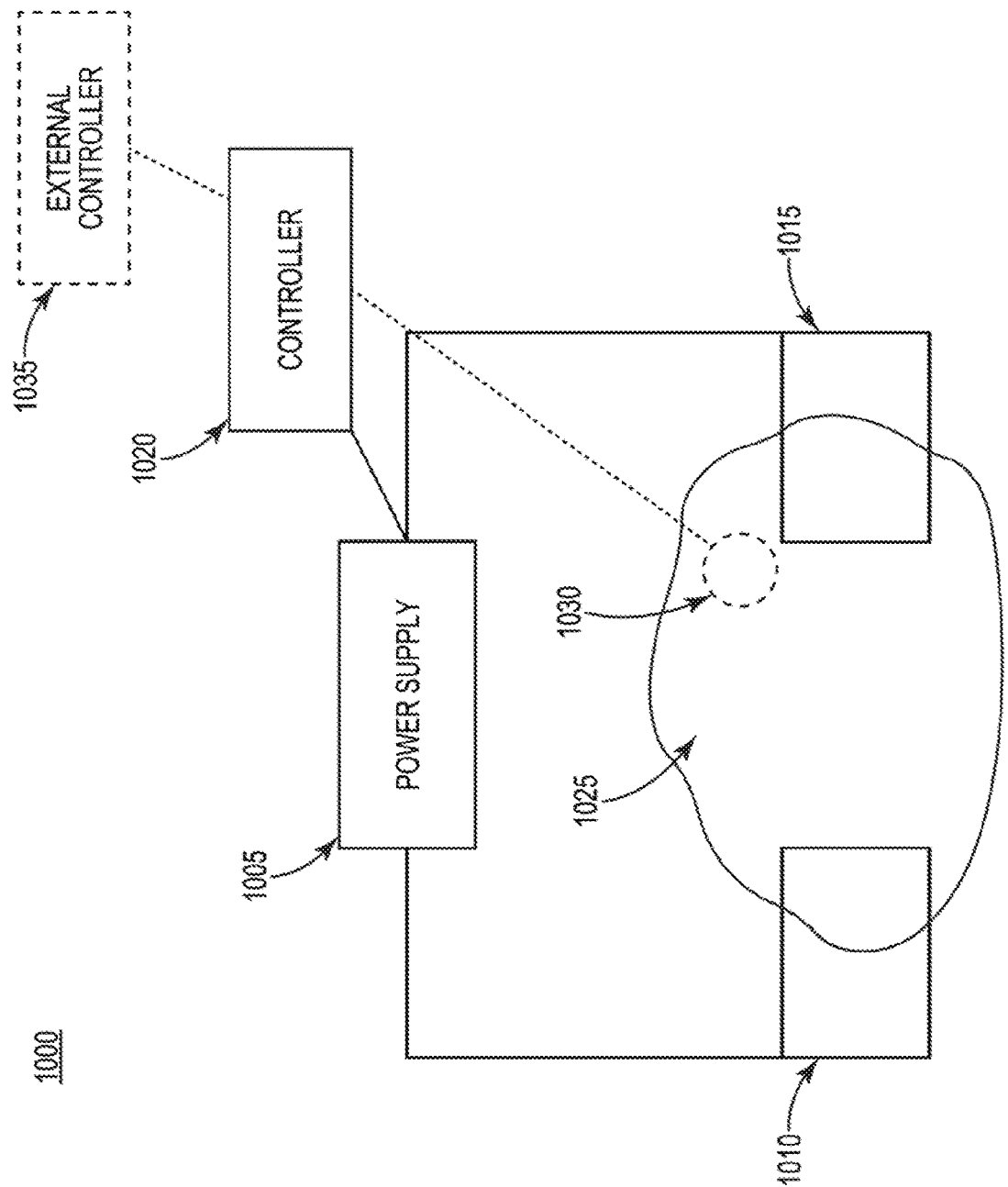
FIG. 1 is a schematic illustration of the electrical circuit according to an embodiment of the disclosure.

FIG. 1 is a schematic illustration of the electrical circuit 1000 which may be used to deliver electrolysis products according to an embodiment of the disclosure. The electrical circuit may include a power supply 1005, two or more electrodes 1010, 1015 coupled to the power supply 1005, and a control system 1020 that may regulate the current and/or voltage through the circuit 1000 or portions thereof. The electrical circuit 1000 may be closed at least in part through an aqueous matrix 1025. The design of the circuit may be such that the current is forced to pass at least in part through the aqueous matrix 1025. The aqueous matrix 1025 may include a manmade material, a biological material, or a combination thereof. The aqueous matrix 1025 may be at a treatment site in direct contact or part of the treatment site. The aqueous matrix 1025 may be the site at which products of electrolysis are generated. The controller 1020 may turn on and of the power to the circuit 1000, may adjust the level of power delivered, and may operate the circuit 1000 in conjunction with other devices. Optionally, the controller 1020 may receive feedback from measurements made in the aqueous matrix 1025 by a sensor 1030. The controller 1020 may also optionally receive signals from an external controller 1035.

Figure 2:
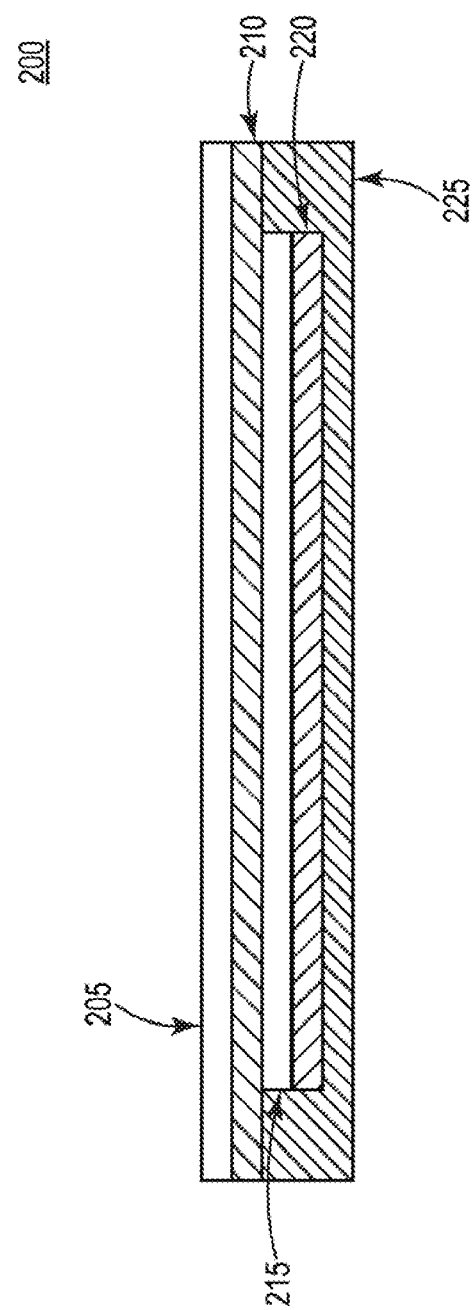
FIG. 2 is a schematic illustration of an apparatus for delivery of electrolysis products to a site according to an embodiment of the disclosure.

FIG. 2 is a schematic illustration of an apparatus for delivery of electrolysis products to a site according to an embodiment of the disclosure. The apparatus 200 may include at least one electrode and an aqueous matrix in contract with the electrode. Generally, the electrode and the aqueous matrix may be selected such that electrolysis products are produced in the aqueous matrix when a current is passed through the aqueous matrix using the electrode. The aqueous matrix may include a manmade material such as a hydrogel and/or a biological material such as tissue. The electrode and aqueous matrix may be packaged for placement the site to which delivery of electrolysis products is desired. In FIG. 2, an electrode 210 and aqueous matrix 225 are shown packaged in a pad 200.

At least one electrode may be included in the apparatus. The electrode 210 is shown in FIG. 2, and may be a cathode in some embodiments. In some examples, however, the electrode 210 may be placed at a location remote from the apparatus, such as proximate another location of a patient's body in some examples. A second electrode may be included in the apparatus, such as the electrode 220 shown in FIG. 2. In some examples, the electrode 220 may be an anode.

Electrode materials are generally selected to include a material that is selected to produce the electrolysis products when a current is passed through the aqueous matrix using the electrode. The materials chosen for the electrodes, including the electrodes 210, 220, may be chosen to produce certain the electrolysis products. For example, an anode (e.g. electrode 220) may include iridium oxide and/or rubidium oxide deposited on titanium, which may improve the production of hypochlorous acid, and a cathode (e.g. electrode 210) may include copper. The use of mixed metal oxide anode electrodes may produce different species of electrolytic products that may be tailored for different clinical needs. The electrodes may also include different materials with properties of interest. For example, platinum may be used if inert electrodes are desired or silver electrodes or silver/silver chloride electrodes if silver ions are desired in the solution, which may further enhance the sterilization effect.

In the example shown in FIG. 2, the electrodes 210 and 220 are separated by an insulating layer 215. The insulating layer 215 may be implemented using any suitable insulating material. In some embodiments, the insulating layer 215 between the electrodes 210, 220 may be omitted. In some embodiments, a portion of the aqueous matrix 225 is between the electrodes 210, 220. In some embodiments, a portion of the aqueous matrix 225 is between the electrode 210 and the impermeable barrier 205.

One or more of the electrodes in the apparatus, such as the electrodes 210 and/or 220 may be externally-accessible for receipt of an electronic signal from a controller, which may be placed remotely from the apparatus, such as the apparatus 200. In some embodiments, the controller may be integrated with apparatus 200.

Apparatuses described herein may include an aqueous matrix in contract with at least one electrode. The aqueous matrix 225 is shown in FIG. 2 in contact with both the electrodes 210, 220. Aqueous matrices described herein, including the aqueous matrix 225, may include components for forming electrolysis products. In some embodiments, the aqueous matrix 225 may be implemented using a gel and/or hydrogel. The aqueous matrix may include a saline solution. The aqueous matrix may have a pH selected to produce electrolysis products, such as hypochlorous acid. In some examples, the pH of the aqueous matrix 225 may range between 2 and 5. The aqueous matrix 225 may be placed in contact with a site for delivery of electrolysis products, such as by laying a pad including the aqueous matrix 225 on the site.

In some embodiments, the aqueous matrix 225 may include a low pH saline solution (e.g. about 3 to 4 pH) that is configured for the production of hypochlorous acid. The materials included in the solution included in the aqueous matrix 225 may be chosen to produce the desired electrolysis products, such as hypochlorous acid). In some embodiments, the aqueous matrix 225 may have a higher electrical conductivity than the site for delivery of electrolysis products. The higher electrical conductivity of the aqueous matrix 225 may result in electrolysis products produced primarily in the aqueous matrix 225, not the tissue at the site. The ionic composition of the aqueous matrix 225 may be designed to have the desired conductivity but to include different ions from those normally in tissue, for example a greater concentration of Na or Ca. In some embodiments, the aqueous matrix 225 may be infused with a drug for combination therapy at the treatment site. That is, both the drug and electrolysis products are delivered to the treatment site.

In some embodiments, aqueous matrices described herein, such as the aqueous matrix 225, may be implemented using a liquid solution. The liquid solution may be prepared separately and applied directly to the treatment site before placement of the impermeable barrier 205. In some embodiments, the treatment pad 200 may be placed at the treatment site and the aqueous matrix 225 may be introduced to the treatment site by injecting it through a port (not shown) in the impermeable barrier 205. In some embodiments, the treatment pad 200 includes a dehydrated gel. Before use, the gel may be hydrated with a solution, such as saline, to form the aqueous matrix 225. In some embodiments, the aqueous matrix 225 is already present in the treatment pad 200. In some embodiments the aqueous matrix is combined with body tissue and/or body fluids.

In some embodiments, the at least one electrode in the apparatus may be coupled to a power supply. For example, the electrodes 210, 220 in FIG. 1 may be coupled to a power supply (not shown). Examples of power supplies may include, but are not limited to, one or more batteries, a computer (e.g., coupled via USB cable), a cellular phone, a regulated power supply that draws energy from the electrical network, a solar cell, and combinations thereof. The power supply may be incorporated in the apparatus, e.g. the treatment pad 200. The power supply generally provides power to one or more electrodes to power the electrolysis process.

The electrode and aqueous matrix may be packaged for placement proximate a site of delivery for the electrolysis products. For example, the electrode and aqueous matrix may be packaged into the pad 200 shown in FIG. 2. In some embodiments, some or all of the components of the pad 200 are disposable. In some embodiments, some or all of the components of the pad 200 are sterilizable. In some embodiments, some or all of the components of the pad 200 may be multi-use.

In some embodiments, the pad 200 is sized to cover a large area of a site. In some embodiments, the pad 200 may have smaller dimensions to limit delivery of electrolysis products to a smaller area. The pad 200 may be implemented in a variety of shapes. For example, the pad 200 may be square, rectangular, circular, ovular, half-moon. Other shapes may also be possible. The shape and/or size of the pad 200 may be selected based on the size and/or shape of the site for delivery.

The pad 200 may include an impermeable barrier 205 which may include a periphery (not shown) that may extend beyond the dimensions of the electrodes 210, 220 and/or aqueous matrix 225. The periphery of the impermeable barrier 205 may include an adhesive that may be used to secure the pad 200 to the site. In some embodiments, the pad 200 is secured by bandages. In some embodiments, the pad 200 is not secured to the treatment site.

While shown packaged as a pad 200 in FIG. 2, a pad may not be used in some examples. In some embodiments, an aqueous matrix may be applied to a site and electrodes applied to the aqueous matrix. For example, it may be desired to treat a confined space between two tissues or inside of one tissue (e.g., a needle hole). The aqueous matrix may be introduced into the confined space, and the electrodes may be inserted into or proximate the confined space. The electrodes may be coupled to a controller and/or low voltage source outside the confined space.

In some examples, ablation by electrolysis may be performed in the interior of a blood vessel or a cavity inside the body. In some embodiments, electrodes may touch a tissue of interest and an ionic flow that propagates by diffusion may be directed towards the tissue of interest. In some embodiments, the flow of ions in an undesirable direction may be impeded by impermeable surfaces. In some embodiments, the direction of flow of ions may be controlled through the use of iontophoresis, electro osmosis and/or electrophoresis.

Example sites include wounds. Examples of wounds that may be treated include but are not limited to bed sores, diabetic ulcers, burns, tears, gashes, surgical incisions, cuts, scrapes, irradiation and scars formation. The pad 200 may accordingly be configured to adhere to the wound. In some embodiments, the apparatuses described herein, such as pad 200, may be used for cosmetic procedures. For example, unwanted cosmetic features may be ablated or the electrolysis products may induce tightening of the skin. Example sites include infected tissue, acne, and/or the pad may be configured for placement on an implantable device (e.g. pacemaker, joint implant, or other medical device). When activated, the pad can then be used to treat an infection proximate the implanted device.

Other example sites for delivery of electrolysis products include a malignant tumor, an abdomen surface, a nerve, a benign tumor, a blood vessel surface, an intestinal surface, an esophagus surface, a urethra surface, a bladder surface, or combinations thereof.

Example apparatuses described herein, such as the pad 200 of FIG. 2, may be packaged for placement proximate a site for delivery of electrolysis products. In this manner, the device may be placed locally to the site for delivery such that the electrolysis products generated by the apparatus may diffuse into and/or be driven toward the site. For example, during operation, the electrodes 210,220 shown in FIG. 2 may be coupled to a power supply, such as a battery. While the pad 200 is applied to the site, the electrodes 210,220 may be energized by power supply, and electrolysis products are formed in the aqueous matrix 225. The electrolysis products may diffuse into the site for an amount of time. A controller (not shown in FIG. 2) may control the coupling of the electrodes 210, 220 to the power supply. The controller may modulate the connection between the electrodes 210, 220 to the power supply to turn on and off current in the aqueous matrix 225, thereby controlling generation of electrolysis products.

In some embodiments, the electrolytic reaction induces a flow of material through the aqueous matrix 225. The flow may extend further into the treatment site. The iontophoretic, electro-osmotic and/or electrophoretic flow may enhance transport of the electrolysis products into the treatment site. This may allow deeper tissue to be treated by the treatment pad 200. In some embodiments, a negative pressure source (not shown) may be used in conjunction with the treatment pad 200 and may be applied to the tissue treated by the treatment pad 200. The negative pressure source may be a tube coupled to a vacuum, a hypobaric compartment, or a manual suction bulb. Other negative pressure sources may be used. The negative pressure source may further enhance production of the electrolysis products at the treatment site and/or remove depleted products and/or ablated materials. In some embodiments, the negative pressure source is manually operated by a user. In some embodiments, the negative pressure source is operated by the controller.

Figure 3:
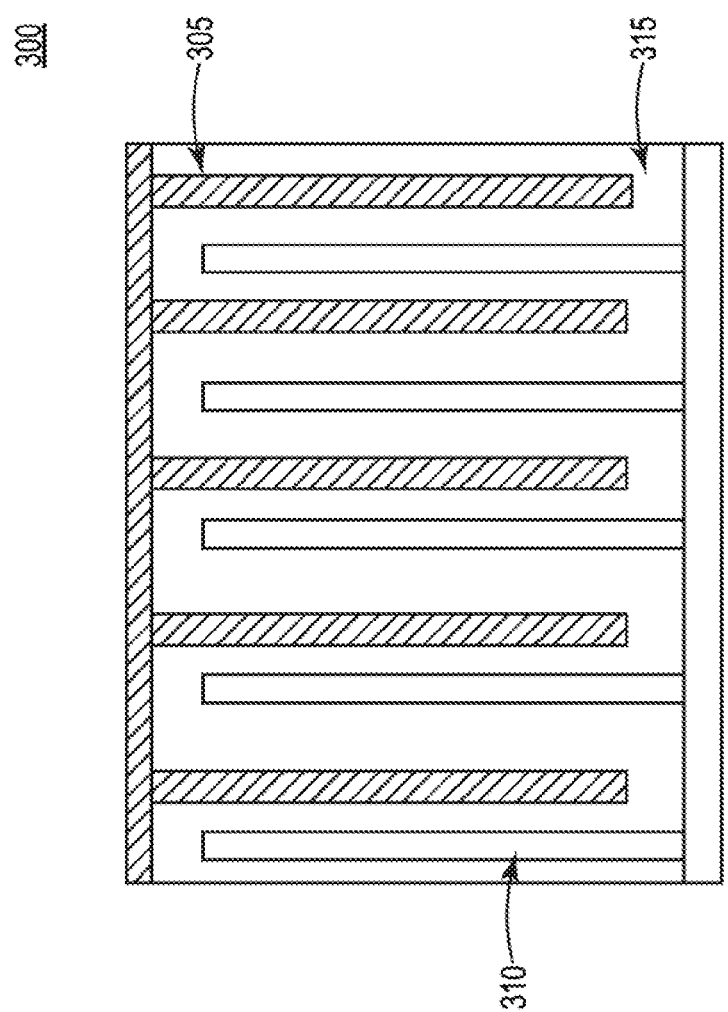
FIG. 3 is a schematic illustration of an arrangement of electrodes according to an embodiment of the disclosure.

FIG. 3 is a schematic illustration of an alternative arrangement of electrodes 300 according to an embodiment of the disclosure. In this arrangement, electrodes 305, 310 may be formed in the same horizontal plane and may be separated by an aqueous matrix 315. In some embodiments, the aqueous matrix 315 may be replaced by a non-conducting film on which the electrodes 305, 315 are sputtered. The film may be embedded in or placed on or in an aqueous matrix.

Figure 4:
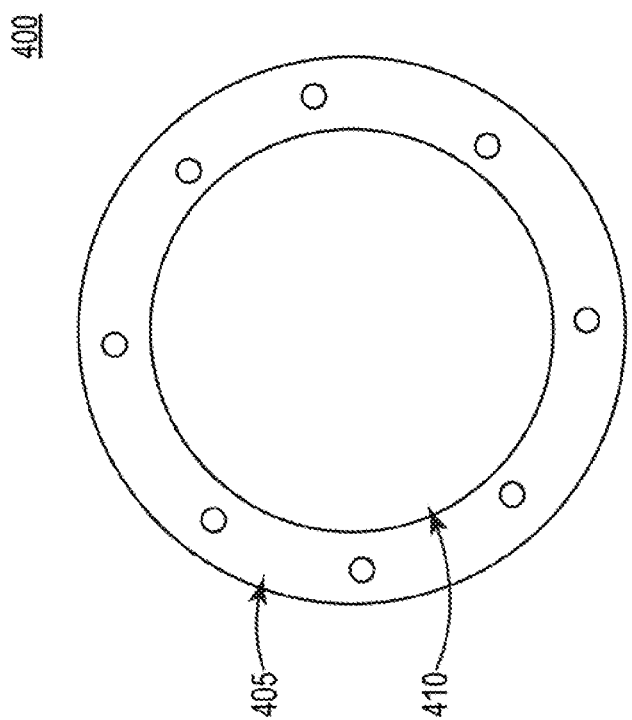
FIG. 4 is a schematic illustration of another arrangement of electrodes according to an embodiment of the disclosure.

FIG. 4 is a schematic illustration of an alternative arrangement of electrodes 400 according to an embodiment of the disclosure. In this arrangement, an anode 410 is disk-shaped and mounted to a disk-shape cathode 405. As shown in FIG. 4, the cathode 405 has a diameter greater than the diameter of the anode 410, however, in some embodiments, the anode 410 may have a diameter greater than the cathode 405. The cathode 405 and anode 410 may have an insulation layer coupled between them (not shown) in some embodiments. In some embodiments, the electrodes 400 are embedded in or placed on an aqueous matrix.

FIGS. 1-4 show various electrode configurations for performing electrolysis. However, these configurations are exemplary, and the disclosure is not limited to these particular electrode configurations and additional electrode configurations may be used. For example, needle electrodes, wire electrodes, and/or surface electrodes may be used. Needle electrodes may, for example, penetrate a tissue to which electrolysis products may be delivered. Surface electrodes may be placed on or near a surface of a tissue to which electrolysis products may be delivered. For example, surface pad electrodes may be used where electrodes are packaged in a pad which is placed proximate (e.g. on) tissue to be treated.

Figure 5:
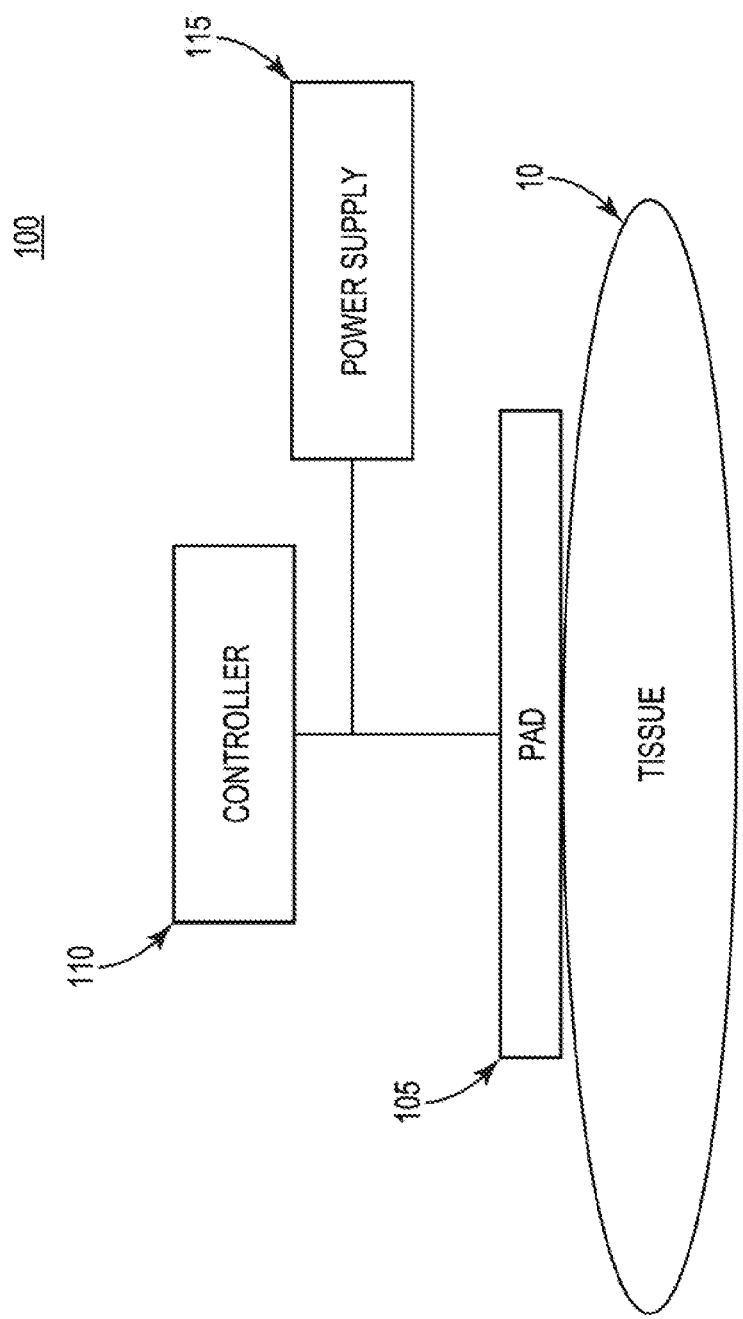
FIG. 5 is a schematic illustration of a system for producing electrolysis products for the treatment of surface of tissue according to an embodiment of the disclosure.

FIG. 5 is a schematic illustration of a system 100 for producing electrolysis products (e.g. electrolytic product), which may be used to deliver electrolysis products to a site, for example for the treatment of a tissue surface according to an embodiment of the disclosure. A pad 105, which may be implemented using the pad 200 of FIG. 2, may be proximate a site that is to be treated (e.g. tissue 10). The pad may be coupled to a power supply 115. An electrical circuit may be implemented through the pad and/or tissue using the circuit in FIG. 1 in some examples. The production and delivery of electrolysis products to the tissue 10 by the pad 105 may be controlled by a controller 110. The controller 110 may, for example, be programmed to provide an electronic signal to the pad 105 and/or power supply 115. The electronic signal may be indicative of a dose of electrolysis products. For example, the electronic signal may control the timing and magnitude of a current generated in the pad 105 to produce electrolysis products. This may allow a user to customize treatment of the tissue 10. For example, the controller 110 may transmit an electronic signal to the pad 105 and/or the power supply 115 to cause the pad 105 to produce a particular flow (e.g. constant flow) of electrolysis products to the tissue 10. In this manner, a controller may be used to electronically control the generation and application of electrolysis products to a site, where the site is proximal an example pad as described herein. Although shown as separate components coupled to the treatment pad 105, in some embodiments, the controller 110 and/or the power supply 115 may be integrated into the treatment pad 105. In some embodiments, the controller 110 may include a programmable chip coupled to the treatment pad 105 and/or power supply 115. In some embodiments, the controller 110 may be implemented using a computing device (not shown) and be remotely coupled to the treatment pad 105. The computing device may be implemented using, for example a desktop, laptop, server, handheld device, a personal computer, a tablet computer, and/or a smart phone. In some examples, the computing device may be integrated with and/or shared with another piece of medical equipment, such as an injection pump, a negative pressure system, or combinations thereof. In some examples, the controller may be programmed to provide an electronic signal indicative of electrolysis product dose and also control the other piece of medical equipment. The controller 110 may be coupled by a wire or communicate with the treatment pad 105 and/or the power supply 115 wirelessly.

The controller may be programmed to provide an electronic signal indicative of a dose of the electrolysis products to an electrode described herein. The controller may, for example, include such a program, or include one or more processing devices (e.g. processors) coupled to a memory encoded with executable instructions for electrolysis product delivery. The controller may cause the current through the electrodes to be pulsed. Other modulation patterns may also be used. The controller may also control the voltage of the power supply in some embodiments. Treatment dosage may also be adjusted by the magnitude of the current applied and duration of energy applied to the aqueous matrix of apparatuses described herein. In some examples, length and/or magnitude of the electronic signal may further indicate a desired depth of the electrolysis product delivery. Generally, a longer application of a current may cause electrolysis products to be produced for a longer time, allowing them to diffuse deeper into the site.

The system 100 may further include a sensor (not shown) for measurement of pH near at least one electrode in the apparatus for delivery of electrolysis products, such as the pad 105. The sensor may sense pH near the electrode and provide the pH value to the controller, such as the controller 110. The controller 110 may further be programmed to adjust an electronic signal provided to the pad 105 and/or power supply 115 based on the pH near the electrode. If the pH varies outside of a predetermined range, additional components may be added to the aqueous matrix to adjust the pH to return it to a range desired for producing the electrolysis products.

Figure 6:
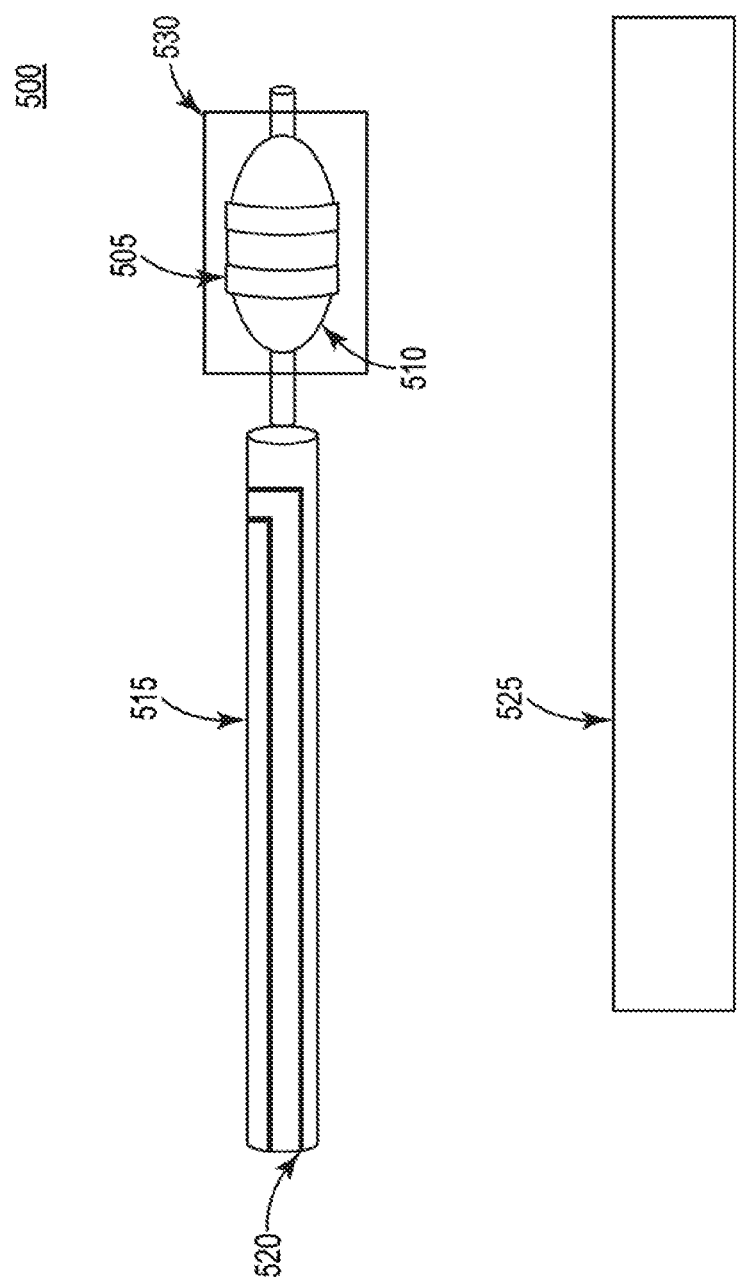
FIG. 6 is a schematic illustration of an internal electrolysis apparatus according to an embodiment of the disclosure.

FIG. 6 is a schematic illustration of an internal electrolysis apparatus according to an embodiment of the disclosure. A balloon catheter 500 may include an electrode 505 deposited or attached to an outer balloon surface 510. The catheter 500 may include a multi lumen shaft 515 that may allow for inflation/deflation of the balloon 510, and one or more electrodes 505 to be coupled via conductors to a power source and/or controller. In some embodiments, the multi-lumen shaft 515 may include one or more fluid transfer lumens 520. In some embodiments the balloon catheter 500 may be inserted or in contact with an aqueous matrix 530 around the electrode 505. The aqueous matrix 530 may include a manmade material, a biological material, or a combination thereof. In some embodiments one or more electrodes may be a remote needle or pad 525, inserted or in contact with a tissue or with the aqueous matrix 530. The aqueous matrix may include a manmade material, a biological material, or a combination thereof. In some embodiments, the fluid transfer lumen 520 may deliver and/or remove fluid substances proximate the electrodes 505. For example, a fluid transfer lumen 520 may deliver a saline solution to the electrodes 505 which may increase the production of hypochlorous acid proximate the target site. In some embodiments, the fluid transfer lumen 520 may remove depleted solution, degraded electrolysis products, and/or ablated tissue from the target site. The addition and/or removal of fluids from the target site may allow for adjustments to the properties of the solution such as pH, ionic composition, and/or dosage. In some embodiments, the removed fluids may be collected and analyzed. For example, the pH of the removed solution may be determined. The pH of the removed solution may determine the composition of new solution delivered to the target site. In another example, the solution may be analyzed for the presence of living microorganisms to determine the effectiveness of a sterilization procedure. Other analysis of the removed solution may also be performed.

In some embodiments, the balloon 510 may prevent the flow of ions from the aqueous matrix 530 in an undesirable direction. This may allow for diffusion of electrolysis products from the aqueous matrix 530 into a vessel wall or other target tissue, causing ablation on the targeted region. In some embodiments, multiple balloons 510 may be included in the catheter 500. The balloons 510 may isolate a target tissue for treatment, which may allow for controlled diffusion of electrolysis products from the aqueous matrix 530 into the target tissue. In some embodiments, the balloon 510 may be ring-shaped. That is, the balloon 510 may include a channel near the middle portion which may allow at least partial flow of fluid through the balloon 510. This may allow the electrodes 505 to contact the target site for electrolysis, but allow for blood flow and/or other fluid flow during treatment.

In some embodiments, the electrode 505 may be deposited on the multi-lumen shaft 515 in addition to on the balloon 510. In some embodiments, the electrode 505 may be deposited on the multi-lumen shaft 515 instead of on the balloon 510. The electrode 505 may be deposited on the multi-lumen shaft 515 upstream and/or downstream from the balloon 510. In some embodiments, when two balloons 510 are included in the catheter 500, the electrode 505 may be deposited on the multi-lumen shaft 515 between the two balloons 510. Other electrode 505 locations may be used.

Figure 7:
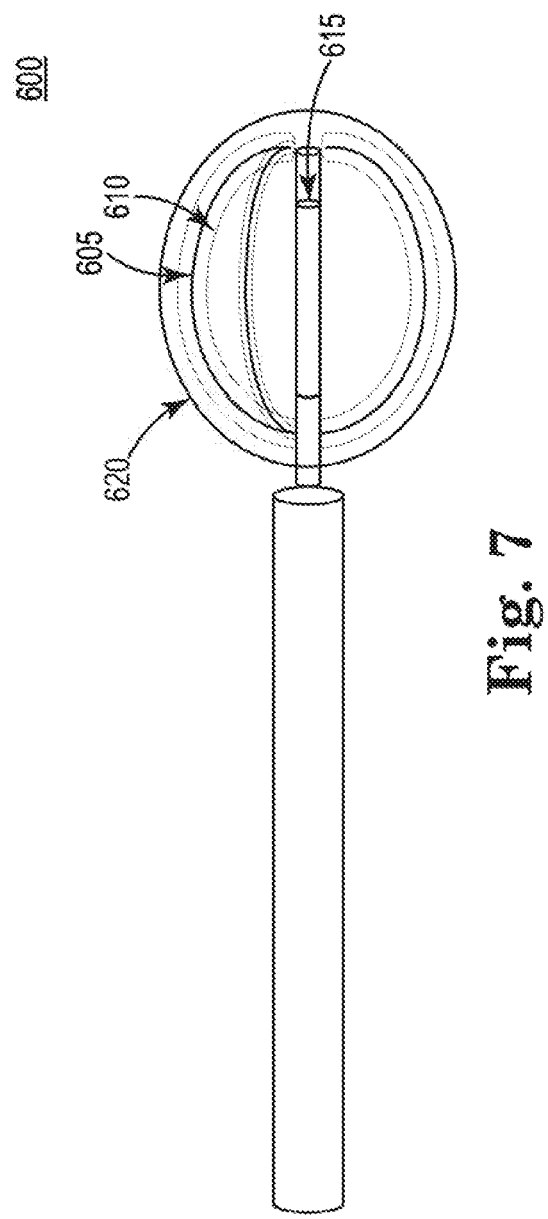
FIG. 7 is a schematic illustration of an internal electrolysis apparatus according to an embodiment of the disclosure.

FIG. 7 is a schematic illustration of another internal electrolysis apparatus 600 according to an embodiment of the disclosure. The apparatus may include a spring electrode 605 design with an impermeable surface 610 attached to the back of the electrodes 605. The spring electrode 605 with the impermeable surface 610 may be embedded in an aqueous matrix 620. The aqueous matrix 620 may include a manmade material, a biological material, or a combination thereof. The impermeable surface 610 may allow for controlled diffusion of electrolysis products from the aqueous matrix 620 into the target tissue. The spring electrodes 605 may be a variety of different shapes and polarities. In some embodiments, the center shaft 615 may incorporate one polarity while the outer spring electrodes 605 are the same polarity and opposite polarity of the center shaft 615. In some embodiments, the apparatus 600 may allow for the application of electrolysis without occluding a vessel, duct, and/or passage.

Figure 8:
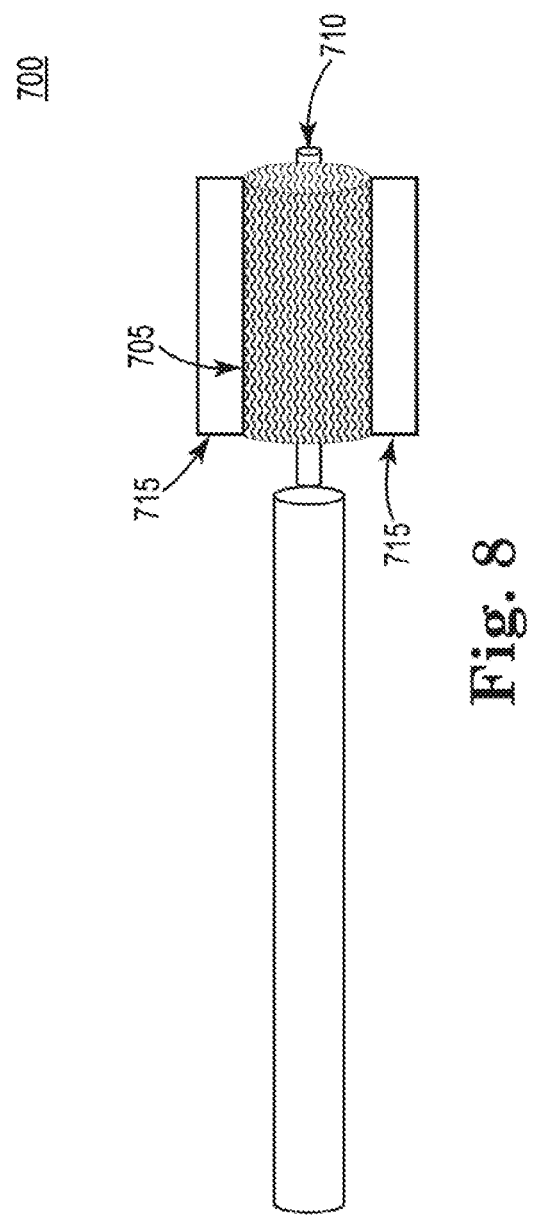
FIG. 8 is a schematic illustration of an internal electrolysis apparatus according to an embodiment of the disclosure.

FIG. 8 is a schematic illustration of another internal electrolysis apparatus 700 according to an embodiment of the disclosure. The apparatus 700 may include a stent 705 embedded in an aqueous matrix 715. The aqueous matrix 715 may include a manmade material, a biological material, or a combination thereof. The stent 705 may have one or more configurations. In some embodiments, the stent 705 may act as an electrode. For example, a wire mesh stent may be used to deliver a low voltage direct current to the tissue. In some embodiments, inner wall of the stent 705 may be coated on one side with the aqueous matrix 715 and on the other side with an impermeable surface which may direct diffusion of electrolysis products from the aqueous matrix 715 into a target site, such as a vessel wall. In some embodiments, the stent 705 may be a nitinol stent that may have the inner surface of the stent 705 coated in a similar fashion. The stent 705 may be configured as either a monopolar electrodes with a shaft 710 as a return, or with a remote second electrode as illustrated in FIG. 6 in a bipolar configuration with both polarities built into the stent 705 but separated by a non-conducting surface. In some embodiments, the impermeable surface may act as a non-conductor to separate the two conducting surfaces on the stent 705.

Figure 9:
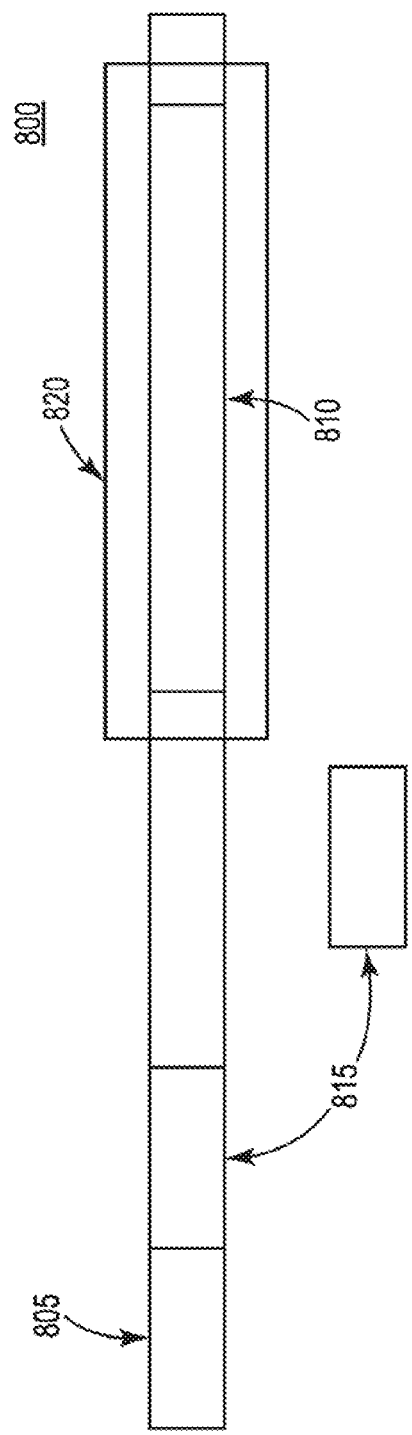
FIG. 9 is a schematic illustration of an internal electrolysis apparatus according to an embodiment of the disclosure.

FIG. 9 is a schematic illustration of another internal electrolysis apparatus 800 according to an embodiment of the disclosure. The apparatus 800 may include a solid insert 805 a portion of which is at least one electrode 810. In some examples, the electrode 810 is an anode. The electrode 810, which may be an anode, may be surrounded by an aqueous matrix 820. The aqueous matrix 820 may include a manmade material, a biological material, or a combination thereof. In some examples, the insert 805 is a needle. A second electrode 815 may be positioned on the surface of the insert 805 and/or in an aqueous matrix surrounding the insert. In some embodiments, the one or more electrodes may be mounted on the outer surface of the insert. The outer surface of the insert 805 may be electrically insulated except for the surface area of the electrodes 810, 815. The apparatus 800 may be directly introduced to the treatment site under imaging (CT. MR, Ultrasound) guidance. An electrical circuit including at least two electrodes and the aqueous matrix 820 may be coupled to a power source (not shown). The power source may be outside the body or inside the body. The power source may be a battery. The power source may be a constant DC current power supply. The treatment may be controlled by a microprocessor (not shown) to determine and deliver dose specific treatment parameters to the targeted treatment site. A treatment planning system may be used to calculate optimal treatment zone placement over the targeted treatment areas to guide placement of the insert electrode.

The internal electrolysis apparatuses illustrated in FIGS. 6-9 may include imaging components. This may allow real time monitoring of electrolysis treatment.

The internal electrolysis apparatuses described above may be used in multiple applications. Examples of applications include targeted lung denervation for chronic obstructive pulmonary disease, renal denervation, and carotid body receptors for congestive heart failure. Another application may involve the use of a balloon catheter with electrodes in the treatment of percutaneous trans luminal coronary angioplasty (PTCA). In this application, an apparatus, for example the apparatus 500, may be used for a traditional angioplasty procedure. The electrodes incorporated on the balloon surface may then be activated pre or post balloon dilation to treat the vessel walls through the production of hypochlorous acid, which may reduce the rate of restenosis. The intraluminal electrolysis allows for treatment of the smooth muscle below the surface which may inhibit the formation of a neointima.

In another application for treatment of restenosis, an apparatus, such as the apparatus in FIG. 8 may be applied to combine the use of a stent with the treatment of intraluminal electrolysis. In this approach, the stent may be placed by conventional means. Intraluminal electrolysis may be applied via the stent which may prohibit restenosis. The intraluminal electrolysis may allow for treatment of the smooth muscle below the surface which may inhibit formation of a neointima.

In another clinical application, intraluminal electrolysis may be used to treat Deep Vein Thrombosis (DVT). An apparatus such as apparatus 500, may be used to combine a catheter based procedure with the treatment of transluminal electrolysis. In this approach, the catheter may be positioned in a normal fashion to dilate the restricted vessel. Before or after dilation, intraluminal electrolysis may be applied, to produce hypochlorous acid to treat the remaining clotted area as well as the surfaces below the vessel wall which may prevent recurrence. The low thermal aspects of the intraluminal electrolysis may make it particularly attractive for this type of application, because of the reduced or non-existent swelling of the tissue as a result of the thermal damage.

In another application for the treatment of DVT, an apparatus, such as apparatus 700 may be used to combine a stent with the treatment of the intraluminal electrolysis. In this approach, the stent may be place in a normal fashion. Intraluminal electrolysis may be applied via the stent in order to treat any remaining clotted area as well as below the surface which may prevent recurrence.

In another clinical application, intraluminal electrolysis may be used to treat Peripheral Artery Disease (PAD). An apparatus such as apparatus 500 may be used to combine a balloon catheter with intraluminal electrolysis. In this approach, the balloon may be placed by conventional means. Intraluminal electrolysis may be applied via the electrodes mounted on the balloon which may treat any remaining plaque as well as the surfaces below the vessel wall which may prevent recurrence.

In another application for PAD, an apparatus such as the apparatus 700 may be used to combine a stent with the treatment of intraluminal electrolysis. In this approach the stent may be placed in normal fashion. Intraluminal electrolysis may be applied via the stent to treat any remaining plaque as well as the surfaces below the vessel wall which may prevent recurrence.

Addition clinical applications of intraluminal electrolysis may include ablation of malignant and benign cell growth on the inner surface of the esophagus (Barrett Syndrome), colon—tumors, rectal tumors, tumors in the mouth, opening of veins for treatment of varicose veins. Intraluminal electrolysis can be utilized inside the heart for ablation procedures that require full transmural lesions. The clinical applications discussed above are exemplary and should not be construed to limit the disclosure to the listed applications.

Some specific experimental examples are provided below to facilitate appreciation of embodiments described herein. The experimental examples presented are not intended to be comprehensive or exhaustive of all experiments performed or of all results obtained.

Example I

In a first non-limiting example, two electrodes of an electrolysis treatment system are configured similar to the electrodes in FIG. 3. The anode is a 1.5-inch (39.4 mm) diameter circle of Titanium, grade 2. It is 0.0005 inches (0.010 mm) thick. The Ti was submersed in iridium chloride and then place in an oven at 450 C for 2 hours. The iridium chloride reacts with the oxygen at high temperatures and a layer of Iridium oxide develops on the titanium and this serves as the anode in our system. An Iridium oxide electrode was used here because it serves as a catalyst to the production of HClO. There may be other materials that catalyze the production of HClO, such as Ruthenium Oxide.

The larger circle with circumferential holes is made of Pyralux (Dupont). It has an outer diameter of 2 inches (53 mm) and a copper layer of 35 microns coated on one side with a high dielectric plastic of 45 micron. The copper surface serves as a cathode. Other materials can be used for cathodes such as Carbon, graphite, graphene, Ag/AgCl. The anode and cathode are attached across the plastic layer, which is used to electrically separate the anode from the cathode. Eight holes of a diameter of 0.085 inches (2.1 mm) are equally spaced at a diameter of 0.2 inches (6.8 mm) The holes serve an important function, as a conduit for the transport of ions between the cathode and anode, which may be generally referred to as a salt bridge. A path for ion transport may be required for the system to function. Two strips extend from the anode and cathode for the purpose of connecting the electrodes to the power supply and the power delivery control system.

The electrodes are then embedded in a gel in the Petri dish. The gel is 0.7 gr. UltraPure Agarose (Invitrogen Cat No. 155510-027) dissolved in 100 ml of distilled water. To maintain a pH of ~4, 590 ml of 1 Molar Citric Acid and 410 ml of Sodium Citrat was introduced. To maintain a physiological saline composition, 9 gr of NaCl were mixed into the solution. The solution was cast in a 2" diameter, Petri dish that served as a mold, in such a way that the electrode assembly was in the middle of the cast. The thickness of the gel is 6 mm.

Wires were coupled to the anode and cathode of the electrode unit. The wires leaving the electrode unit are connected to an Agilent E3631A constant current power supply. A top gel layer of a Methyl Violet (Fluka) dye infused agar gel, was set on top of the electrolysis gel in which the electrode unit was embedded to serve as a measurement marker for the production of hypochlorous acid. The thickness of the measurement marker gel is 7 mm and the diameter is 2 inch. Methyl Violet is denatured by hypochlorous acid and turns clear. As hypochlorous acid is produced at the anode and diffuses into the Methyl Violet dye gel layer, the gel becomes clear where the HClO has interacted with the Methyl Violet. The bottom gel is a pH sensitive dye infused agar. The thickness of the gel is 7 mm and the diameter is 2 inch (53 mm). Whenever a basic or acid solution interacts with the dye a color change occurs. Hydroxides produced at the cathode, turn this gel into a blue color.

A voltage of 4 V, (98+/−8 mA) was applied for 10 minutes across the electrodes. Knowing the time and the charge delivered, as well as the pH of the gel, allows a calculation of the amount of free chlorine produced by this system. In this case, It was calculated that approximately 35 mg of free chlorine was produced over the 10 min period. The ability to calculate the electrolysis products may facilitates a precise quantitative and temporal delivery of the disinfection species. Chlorine gas bubbles may form on the anode. These bubbles may be trapped in the gel of the pad, between the anode and the gel. Because they are trapped and the chlorine produced species diffuse away into the treatment target, the amount produced during these 10 minutes of operation may be completely utilized, which may facilitate precise quantitative delivery of hypochlorous acid. In contrast, in systems that employ HClO solutions in the form of a fluid open to the atmosphere, the active compounds can evaporate and dissipate. After 10 min of activation, hypochlorous acid induced denaturation of the methyl violet dye at the interface between the electrolytic gel and the Methyl Violet stained gel. The copper on the back oxidized, but continued to work. There was no leakage, and very little hydroxide was produced. To avoid this oxidation, the cathode could be made of other materials such as carbon.

Following 10 minutes of activation the current was stopped and the electrolytic pad was allowed to remain in place for another 30 minutes. After 40 minutes of application, of which only 10 minutes were active, the penetration of HClO and the discoloration is much larger that after the 10 minutes of activation. The gel pad may trap all the electrolysis products in the gel pad assembly. After 10 minutes activation all the products are still in the gel. The pH of 4 of the gel may assure that the products are primarily hypochlorous acid. The gel continues to supply the precise quantity of hypochlorous acid embedded in the gel. Thirty minutes after the electric activation of the pad has stopped, the hypochlorous acid continues to penetrate the methyl sample. However the amount delivered may be precise.

There was little change in the pH dye gel facing the cathode. Except in some corners that may have been a result of leakage from the anode side. This indicates that this particular design favors the production of HClO at the anode, facing the treatment site.

Another experiment with the Methyl violet test pad with another design configuration. In this design configuration the gel pad with the electrodes was kept in the Petri dish, allowing only the anode side to be in contact with the test pad. The cathode side was in contact with the Petri dish wall. In this experiment the electrodes were activated for 20 minutes with a voltage of 4V and a current of 118 mA, for a calculated total of 70 mg free chlorine. The treated pad became transparent. The electrolysis device produced complete saturation of the treated pad, throughout the treated pad after 20 minutes of activation.

Example II

In a second non-limiting example, experiments employed a large 6" (153 mm) Petri dish. A hole with a diameter of 3.5" (88 mm) was cut through the back of the Petri dish, to allow access to the precision electrolysis pad and to negative controls. The precision electrolysis pad was placed inside the hole. In this design the cathode side was covered with an impermeable coating. The two electrodes of the pad were connected to an Agilent E3631A constant current power supply.

The large 6 inch (153 mm) Petri dish was filled with physiological agar (1 gram tryptone, 0.5 g yeast, 0.9 g NaCl, 1.5 g Agar per 100 mL) to allow growth of $E. coli$ of an antibiotic resistant strain, ATCC 55244. The height of the gel, from the bottom of the Petri dish was 5 mm. The hole in the back of the Petri dish allowed contact with the active (anode) side of the electrolysis pad and to the negative controls of: a) Gauze saturated with Anasept (HClO containing fluid), b) Allevyn—silver dressing, c) Procellera wound pad (self-powered galvanic system generating Ag and Zn ions). The electrolysis pad anode side, was placed flush with the inner surface of the Petri dish, in good contact with the gel.

A positive control was also prepared. The Petri dish had a 5 mm high agar gel as described earlier. As in all the experiments, a thin layer of $E. coli$ ATCC 55244 was spread on the top of the gel, on the surface opposite to the surface in contact with the bottom surface of the Petri dish. The control was left outside on the bench at room temperature for 50 minutes, similar to the protocols in which active sterilization was attempted. It was then placed overnight, for 18 hours, in an incubator at 37 C.

In the electrolysis experiments, the electrode pad was placed as described previously. As in all these experiments, a thin layer of $E. coli$ was spread on the top agar plates surface. Electrolysis was generated by passing a voltage of 4 Volts (approximate current was 50-60 milliAmps) through the electrodes for 20 minutes. Then the electrolysis pad was left in situ for 30 more minutes. Following the experiments all plates were collected and placed in an incubator overnight for 18 hours at 37 C. A region in which there was no $E. coli$ growth formed in relation to the hole at the bottom of the Petri dish where the electrolysis pad was present. It was evident that the sterilization of the bacteria occurred within the outline of the anode on the pad. The pad was placed on the back side of a surface contaminated with $E. coli$. The distance between the pad and the contaminated surface was 5 mm. This suggests the electrolysis pad may have the ability to sterilize deep in the body.

A first negative control study was performed by using in the same experimental configuration with a gauze saturated with a commercial HClO product (Anasept). The pad was placed on the part of the gel with the hole, in a similar way to the placement of the precision electrolysis pad. The use was according to the manufacturer recommendations. Similar to the previous experiments, the $E. coli$ was spread on the surface of the gel opposite the placement of the Anasept saturated gauze. The saturated gauze was kept in place for 50 minutes, after which the plates were collected and placed in an incubator for 18 hours at 37 C. Several large $E. coli$ colonies grew on the surface opposite the hole on which the gauze was placed.

A second negative control study was performed with a commercial product that employs a silver ion dressing, Allevyn. The Allevyn pad was placed on the surface of the gel facing the hole, as with the other experiments. The pad was applied according to the manufacturer instructions. The Allevyn pad was kept in place for 50 minutes, after which the plates were collected and placed in an incubator for 18 hours at 37 C. The part of the gel facing the hole was completely covered with $E. coli$ growth.

A third negative control study was performed with a commercial product that employs galvanic decomposition of Zn and Ag electrodes, Procellera. The process here is driven by the difference in electrochemical potential of Ag and Zn, and a galvanic, self powered, electrolytic reaction. The Procellera pad was placed on the surface of the gel facing the hole, as with the other experiments. The Procellera pad was applied according to the manufacturer instructions. The Procellera pad was kept in place for 50 minutes, after which the plates were collected and placed in an incubator for 18 hours at 37 C. The part of the gel facing the hole was completely covered with $E. coli$ growth.

The above experiments demonstrate the function of the electrolytic pad and the advantage of this design over other sterilization configurations and systems. It is evident that while the electrolysis pad was able to sterilize antibiotic resistant $E. coli$ at a penetration of 5 mm from the applied surface, the three negative controls tested, using the manufacturer instructions, were unable to effectively destroy the microorganisms at a depth of 5 mm from the placement of the pads. This result illustrates a major problem with the current treatment of wound infections. It is evident that the current methods may not sterilize bacterial infection in the wound depth. Sterilization on the wound surface—without penetrating the depth leaves open a possible source of contamination. The electrolysis technology may have the ability to sterilize deep into tissue, which could be particularly beneficial for deep infections.

Example III

Figure 10:
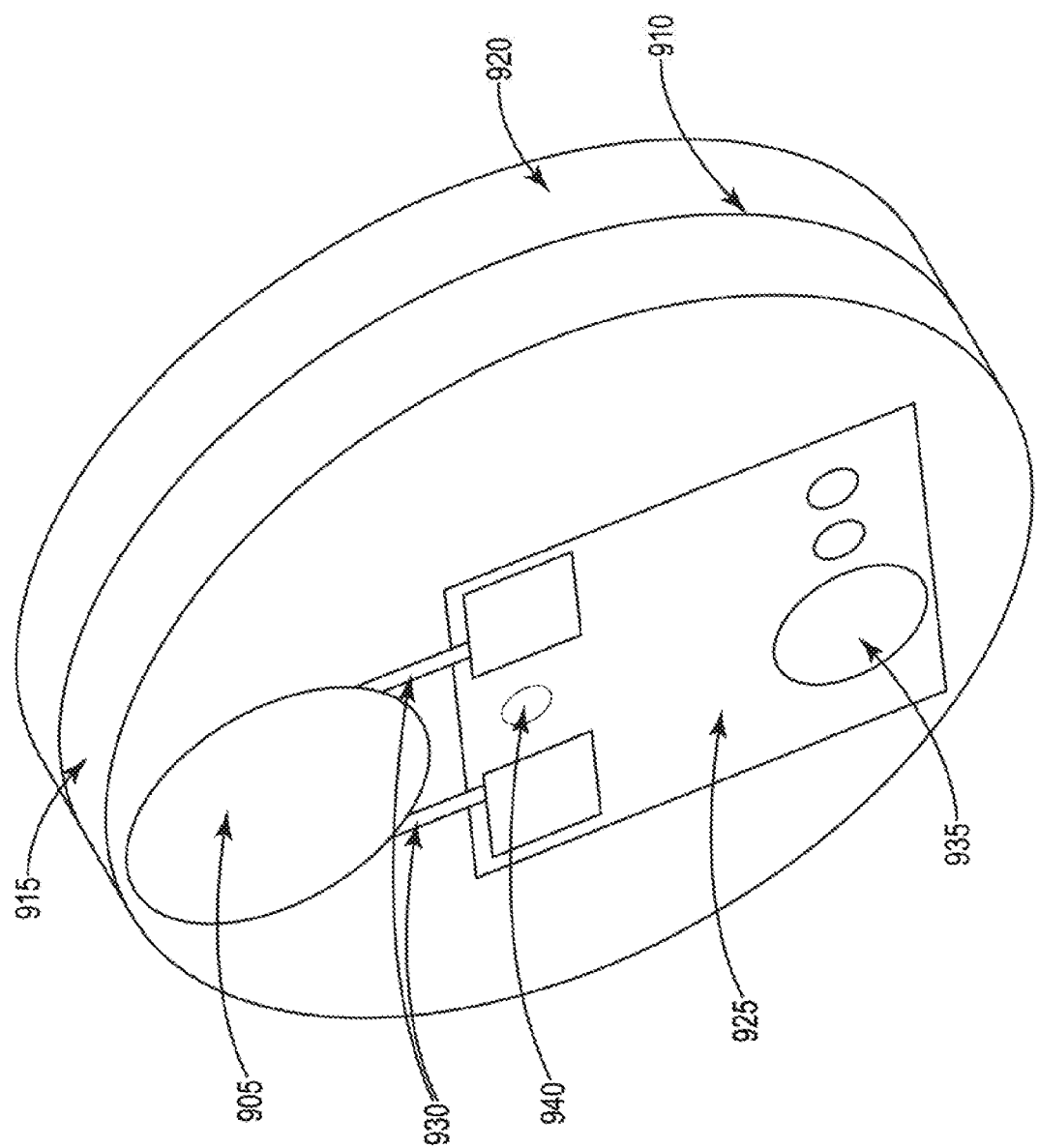
FIG. 10 is a schematic illustration of a pad in accordance with an embodiment of the disclosure.

For a third non-limiting example, FIG. 10 illustrates a precision electrolysis pad 900 in accordance with an embodiment of the invention. The precision electrolysis pad may include all the elements in the same device. The precision electrolysis pad 900 may be provided in a container that is sealed and keeps the precision electrolysis pad 900 sterile until opened for use. The container may be a vacuum sealed bag or other suitable container.

FIG. 10 is a view of the pad 900 from the side that may come into contact with a wound. The two-electrode unit 905, similar to electrode 400 in FIG. 4, is shown with the anode surface visible, the anode surface may be similar to anode 410 in FIG. 4. All the components are on plane 910, embedded between two gel cylinders 915, 920. The gel cylinders 915, 920 may be made of agar gel or a hydrogel or any type of material that includes a saline solution and a pH buffer. The pH buffer may maintain a pH of between 2 and 6, preferably between 3 and 5, preferably 4. The gel may be 1.5 grams UltraPure Agarose (Invitrogen Cat No. 155510-027) dissolved in 100 ml of distilled water. To maintain a pH of ~4, 590 ml of 1 Molar Citric Acid and 410 ml of Sodium Citrat may be used. Nine grams of NaCl were mixed into the solution to maintain salinity. The outer dimension of each gel cylinder 915, 920 may be 2 inches (53 mm) and the thickness may be 0.23 inches (6 mm).

The electronic components of the device may be assembled on a solid surface 925. The solid surface 925 may be connected to the electrodes 905 through electrical connections 930. A programmable microprocessor 935 may turn on and off the electric current may be mounted to the solid surface 925. The programmable microprocessor 935 may be a Bluetooth device that may be controlled from the exterior or a programmable chip or a simple on/off switch. In some embodiments, precision electrolysis electrodes 905 may be a separate unit or an integrated unit as shown in FIG. 9. The power supplied to the electrodes may come from a stationary power source or from a portable power source that may also be another pad connected to the electrodes 905 by an electric wire. To verify that the unit is operational an LED 940 may be run in parallel with the connections 930. The power supply may be a battery. A battery (not shown) may be mounted to the opposite side of the solid surface 925. The battery may be a 3 Volt Lithium battery (Cr2032).

Example IV

The precision electrolysis concept may be implemented with other designs as well. The electrolytic process may be performed at the treatment site and precision may be accomplished through placement of the electrodes at the desired location, control over the pH environment, and active control of the passage of current to generate the desired electrolysis products at the site.

In a fourth non-limiting example, a Petri dish was filled with a physiological solution based agar gel with Kanamycin. To contaminate the surface, an antibiotic resistant *E. coli* strain (ATCC Product No. 55244) was used, which was spread evenly on the agar gel. The sterilization was performed using a physiological saline gel pad with a pH of 4 designed composition similar to that in the previous experiments. However, here the electrodes were two 0.7 mm diameter cylindrical electrodes made of carbon inserted vertical into the pad and not along the pad as previously described. The gel pad sterilization was activated with input from a constant voltage power supply connected to the two electrodes First the gel pad was applied on a contaminated surface of the Petri dish for one minute without activating the electrodes. The pad was then removed and transferred the dish to an incubator for 36 hours in conditions most amenable for bacteria growth, at 37 C. The dish was then removed. In the second experiment the gel pad was applied as in the first experiment, but the gel was activated at specific predetermined areas with two carbon electrodes, for a one minute activation of 20 V. The gel pad was then removed and the samples placed in the incubator for 36 hours.

The gel pad was infused with a pH sensitive dye. The activated area was shown through a change of color in the pad, as a function of the change in pH. A yellowish original color of the pad indicated a pH of 4. When electrolysis occurred, the color of the activated part of the pad changed, according to the change in pH. This aspect of the gel pad may allow the users to know immediately if the electrolysis activation is successful or not and the site of activation.

After the one minute activation the gel pad was removed and the Petri dish incubated for 36 hours. After 36 hours the bacteria grew well across the entire petri dish. However, at areas in which gel pad was activated there was no spread of bacteria. This study may illustrate the feasibility of and the characteristics of a precision electrolysis active and controlled sterilization gel pad. It illustrates different designs may be possible to accomplish the desired precision electrolysis.

The examples provided are for explanatory purposes only and should not be considered to limit the scope of the disclosure.

The electrolysis apparatuses, devices, and systems described above and illustrated in FIGS. 1-9 may be used alone or in combination with other therapies. For example, precision electrolysis may be performed in conjunction with thermal ablation in some applications. In some applications, cells targeted for ablation may be permeablized before, after, or during electrolysis. Examples of devices, pads and permeabilizing techniques are described in co-pending PCT Application Serial No. PCT/US2014/065794, filed Nov. 14, 2014, entitled "METHODS, SYSTEMS, AND APPARATUSES FOR TISSUE ABLATION USING ELECTROLYSIS AND PERMEABILIZATION," which application is incorporated by reference herein in its entirety for any purpose.

The cells may be sonoporated, electroporated, or chemically permeablized. In the case of electroporation, the same electrodes used for electrolysis may also be used for electroporation in some embodiments. In some embodiments, the electrodes for electroporation and electrolysis are separate. The permeabilization of the cells may increase the diffusion of electrolysis products into the cells. The combination of therapies may increase the effectiveness of the electrolysis.

It is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present devices, apparatuses, systems, and methods and should not be construed as limiting the appended claims to any particular embodiment or group of embodiments. Thus, while the present disclosure has been described in particular detail with reference to exemplary embodiments, it should also be appreciated that numerous modifications and alternative embodiments may be devised by those having ordinary skill in the art without departing from the broader and intended spirit and scope of the present disclosure as set forth in the claims that follow. Accordingly, the specification and drawings are to be regarded in an illustrative manner and are not intended to limit the scope of the appended claims.

What is claimed is:

1. A method for delivering electrolysis products to a site, the method comprising:
   using a controller, generating an electrical signal indicative of a timing and dose of the electrolysis products, wherein the electrolysis products are configured to cause ablation;
   providing the electrical signal to a device proximate the site;
   applying a current proximate the site by the device responsive to the electrical signal;

causing a portion of aqueous matrix proximate the site to generate the electrolysis products proximate the site responsive to the current; and controlling at least one of a magnitude or a duration of the current to modulate an amount of the electrolysis products.

2. The method of claim 1, wherein the device comprises at least one electrode and an aqueous matrix, wherein the electrolysis products are generated in the aqueous matrix responsive to the electrical signal applying a current through the aqueous matrix.

3. The method of claim 2, further comprising delivering a drug to the site, wherein the drug is included with the aqueous matrix.

4. The method of claim 2, further comprising:
sensing a pH value in the aqueous matrix between the electrode and the site;
providing the pH value to the controller; and
adjusting the electrical signal responsive to the pH value.

5. The method of claim 4, further comprising adding additional components to the aqueous matrix to adjust the pH if the pH value is outside a predetermined range.

6. The method of claim 2, wherein the at least one electrode and the aqueous matrix are packaged for placement proximate the site.

7. The method of claim 1, wherein the device comprises a pad, and wherein the method further comprises applying the pad to the site.

8. The method of claim 1, wherein the device comprises a pad, and wherein the method further comprises implanting the pad proximate the site.

9. The method of claim 1, wherein the device comprises one of a surface pad, luminal catheter, or a needle.

10. The method of claim 1, wherein using the controller comprises accessing a memory storing electrical signal patterns suitable for particular doses and depths of electrolysis product delivery.

11. The method of claim 1, wherein the site comprises a bed sore, a diabetic ulser, a burn, acne, a tumor, an abdominal surface, a nerve, a blood vessel surface, an intestinal surface, an esophageal surface, a urethra surface, a bladder surface, or a combination thereof.

12. The method of claim 1, wherein the electrical signal is to control timing and magnitude of a current to produce the dose of the electrolysis products.

13. A method for delivering electrolysis products to a site, the method comprising:
passing a current through an aqueous matrix, wherein the aqueous matrix is configured to produce electrolysis products responsive to the current, wherein the electrolysis products are configured to cause ablation; and
modulating an amount of the electrolysis products produced by a portion of the aqueous matrix responsive to controlling at least one of a magnitude or a duration of the current applied to the portion of the aqueous matrix.

14. The method of claim 13, further comprising generating the current by applying an electrical signal to at least one electrode.

15. The method of claim 14, wherein the electrical signal is a pulsed electrical signal comprising one or more pulses.

16. The method of claim 14, wherein the at least one electrode and the aqueous matrix are packaged for placement proximate the site.

17. The method of claim 13, further comprising controlling a direction of flow of ions of the electrolysis by performing iontophoresis, electro osmosis, electrophoresis, or a combination thereof.

18. The method of claim 13, further comprising removing depleted electrolysis products, ablated materials, or a combination thereof from the site.

19. The method of claim 18, wherein the removing comprises applying a negative pressure to the site.

20. The method of claim 18, wherein the removing is performed by a lumen of a catheter.

21. The method of claim 13, wherein controlling at least one of the magnitude or the duration of the current comprises turning the current on and off.

22. The method of claim 13, further comprising measuring a pH of the site.

23. The method of claim 22, wherein the controlling at least one of the magnitude or the duration of the current is performed responsive the pH measured.

24. The method of claim 13, wherein the current comprises a direct current.

25. The method of claim 13, further comprising delivering the aqueous matrix to the site by injection, implantation, or a combination thereof.

* * * * *